United States Patent [19]

Nobbs et al.

[11] Patent Number: 4,799,453

[45] Date of Patent: Jan. 24, 1989

[54] APPARATUS FOR THE SOLIDIFICATION OF LIQUID FILMS

[75] Inventors: James H. Nobbs, Bardsey; Peter K. T. Oldring; David Duerden, both of Morpeth, all of England

[73] Assignee: Thomas Swan & Co., Ltd., Durham, England

[21] Appl. No.: 90,066

[22] Filed: Aug. 27, 1987

[30] Foreign Application Priority Data

Aug. 28, 1986 [GB] United Kingdom ............... 8620807
Nov. 4, 1986 [GB] United Kingdom ............... 8626350

[51] Int. Cl.⁴ ............................................. B05C 11/00
[52] U.S. Cl. ..................................... 118/665; 118/33; 118/101; 118/641; 118/712
[58] Field of Search ................. 118/665, 33, 101, 641, 118/712

[56] References Cited

U.S. PATENT DOCUMENTS 2,335,235 11/1943 Clifton ............................. 265/12
2,817,727 1/1958 Euverand ........................ 73/78
3,785,198 1/1974 Heetman ......................... 73/81

FOREIGN PATENT DOCUMENTS 633586 11/1947 United Kingdom .

Primary Examiner—Bernard Pianalto
Attorney, Agent, or Firm—Bromberg, Sunstein & Casselman

[57] ABSTRACT

The solidification characteriztics of a solidifiable liquid film are monitored by effecting relative movement between a stylus and the film and monitoring the resistance to movement of the stylus through the film as the film is solidifying. The film may be subjected to ultraviolet radiation or elevated temperature to cause solidification. The resistance to movement may be monitored electrically in which case it may be recorded as a trace or a chart recorder.

7 Claims, 11 Drawing Sheets

APPARATUS FOR THE SOLIDIFICATION OF LIQUID FILMS

This invention relates to the solidification of liquid films.

It is frequently desirable to be able to monitor the rate at which liquid films in the form of, for example, surface coatings, paints, inks, lacquers, printer circuit board resists etc., reach their solidified state when, for example, carrying out quality control tests on such materials and formulating new materials. Hitherto, the techniques used have involved assessing the swab resistance of the film by applying a solvent (such as methylethylketone or xylene) to the film by means of a swab or manually testing the film by means of the thumb and such techniques are somewhat inaccurate. It is also known to obtain a measure of the drying characteristics of a liquid film by drawing a stylus through the film and observing the rate at which the film tends to flow back and obliterate the trace left by the stylus as it is drawn through the film. Again, this technique has limited accuracy.

Traditional films often take an appreciable time to solidify even when accelerated drying techniques (e.g. ovens) are used but the newer systems (e.g. those making use of radiation curing) typically solidify in less than 0.1 second. This high rate of cure represents problems when attempting to differentiate between the effectiveness of different film formulations. In order therefore to ensure that proper curing does occur, many commercial suppliers of ultraviolet radiation cured compositions for forming films tend to include, in the compositions, large excesses of photoinitiators and the like and this is not desirable.

It is an object of the present invention to enable the rate of drying of liquid films to be monitored with some accuracy under laboratory conditions.

According to one aspect of the present invention there is provided a method of determining the solidification characteristics of a solidifiable liquid film coated onto the surface of a substrate which method comprises:

(i) penetrating said liquid film with a stylus so that it contacts said surface;

(ii) effecting relative movement of the stylus and said surface so that the stylus moves with respect to and through said film whilst the film is solidifying; and (iii) measuring the resistance to movement of the stylus through the film to obtain a measure of the solidification characteristics of the film.

According to another aspect of the present invention there is provided an apparatus for monitoring the solidification characteristics of a solidifiable liquid film coated onto the surface of a substrate which apparatus comprises:

(i) a means of supporting the coated substrate whilst the film is solidifying;

(ii) a stylus mounted so as to penetrate the liquid film and contact the surface of the substrate;

(iii) a means of effecting relative movement between the stylus and the substrate so that the stylus moves with respect to the surface of the substrate and through the film whilst the film is solidifying; and (iv) a means of monitoring the resistance to movement of the stylus through the film to obtain a measure of the solidification characteristics of the film.

The essence of the invention relies in monitoring the change in the rheological properties of the film as it solidifies by measuring the resistance to motion of the stylus as it moves with respect to and through the liquid film during solidification of the film. Generally, the relative movement between the stylus and the film will be uniform and the speed of this movement will be determined in dependence upon the nature of the material constituting the film and the type of solidification involved, so that when carrying out the determination the stylus moves through film which is still wet and also film which has been solidified.

It may be necessary to apply a downward force to the stylus in order to obtain significant differences in resistance. This force may be, for example, from 100 to 1000 grams depending upon the particular circumstances such as the nature of the substrate, the film weight, the technique used to detect the resistance to movement, and the nature of the mechanism by which the film solidifies.

The invention is suitable for determining the solidifying characteristics of a large variety of different types of solidifiable films including both convertible and non-convertible films. Thus, for example, it is suitable for monitoring films which solidify as a consequence of being subjected to ultraviolet or infrared radiation or an electron beam, oxidation (e.g. films based on alkyd resins), heating (e.g. phenolic resins films), chemical reaction between reactive groups (e.g. epoxy resin based films), free radical formation (e.g. films which solidify after peroxide initiation), evaporation (i.e. films formed by removal of a liquid phase from a solution or emulsion), precipitation i.e. films of, for example, ink formed by changing the solvent balance of a solution so as to precipitate out a solid phase, etc. For simplicity, the solidification of all such films is referred to hereinafter as "curing".

Thus, the invention has many applications such as, for example, monitoring the drying of inks during printing, the curing of U/V curable (slow and fast) optical fibre coatings and the hardening of adhesives and paints. Also, the invention enables the influence of the substrate on the solidification characteristics of the film to be assessed.

Any suitable liquid film thickness may be used and a thickness of from 1 to 500 microns is typical and the substrate used can be selected from a wide range. The film may be applied to the substrate by any conventional means.

In the case where the film is not self-curing, it will be necessary to provide an environment which is such as to promote the curing. Thus, for example, the apparatus may include a means of subjecting the film to ultraviolet or infrared radiation or a thermostatically controlled means of increasing the temperature of the film.

In the case where a means of irradiating the film is used, the invention can be used to differentiate between films which cure rapidly in the presence of such radiation by reducing the amount of radiation received by the film so as to increase the cure time and thereby enable differences in cure time to be measured under laboratory conditions. It has been found that there is correlation between such differences and the differences which are found under commercial conditions. The radiation used needs to have a wavelength which is appropriate to the film material being used. Ordinarily, for example, in the case of ultraviolet radiation induced curing, the radiation will have a wavelength of 254 nm and/or 365 nm.

By providing a range of apparatus in accordance with the present invention including different types of means for promoting curing, the rate of cure of many of the traditional film materials and of the newer film materials can be determined. Further, if desired, the apparatus of the present invention may include a means of supporting a plurality of coated substrates and a means of moving a separate stylus through each film so that a number of samples can be simultaneously tested and prepared.

The apparatus may be such as to enable the cure time to be varied from as little as 1 second to as long as a day or more depending upon the nature of the film. Also fans can be incorporated if it is desired to simulate air flow during the curing of the film.

In accordance with one form of the invention, the stylus is moved and the coated substrate is stationary. In this case, the stylus may be mounted on a carriage adapted to be moved by means of, for example, a screw thread or by means of a wire or inextensible belt. In order to ensure smoothness of motion, the carriage will ordinarily be supported by one or more guide rails and the motor used to move the carriage is preferably a variable speed motor which can be pre-set at any given speed. The stylus will generally be formed of metal and may be, for example, in the form of a stainless steel pointer having a spherical end adapted to contact the surface of the substrate so as to ensure that this contact is vertical.

In one embodiment, the stylus is resiliently supported on the carriage by means of a spring. In this case, the carriage can be moved by, for example, a screw thread or by a wire or inextensible belt. As the stylus is propelled through the film by the moving carriage, the deflection of the spring as a consequence of the resistance encountered by the stylus may be detected by means of a pointer attached to that end of the spring adjacent to the stylus. Alternatively, and more preferably, the deflection of the spring is monitored electrically. In this case, the deflection of the spring can be detected by providing for example strain gauges connected to either side of the spring or by making use of the piezoelectrical effect. In another technique, a magnetic displacement method can be used by, for example, connecting a magnet to the bottom of the spring and obtaining an electrical signal by means of the Hall effect. In another form of the invention, the deflection of the spring may be detected optically by, for example, the deflection of a beam of light reflected from a mirror attached to the stylus.

If desired the resistance to movement of the stylus can be determined as a function of the variation in force of the means used to move the carriage. Thus, instead of resiliently mounting the stylus on the carriage, the stylus may be directly connected to the carriage with the carriage being driven by means of a wire or inextensible belt passing over a resiliently mounted pulley. In this case, the resistance to movement of the stylus through the film causes axial movement of this pulley and this axial movement can, for example, again be detected electrically by means of, strain gauges or piezoelectrically or by the Hall effect or be detected by an optical displacement technique.

In a further embodiment, instead of measuring the tension in the drive mechanism for the carriage, the resistance to movement of the stylus through the film is determined by monitoring the load on the motor used to drive the carriage. As the resistance to motion increases, there will be a change in the load. This technique can be used in the case where the carriage is moved by means of a wire or inextensible belt or by means of a screw thread.

In accordance with another form of the invention, the coated substrate is moved and the stylus is stationary. Generally, this form is preferred since it facilitates access to the illumination source. In this case, the stylus may be mounted in a holder supported so as to be able to move vertically. A tensioning force is applied to the holder so as to cause the stylus to penetrate the film. The tensioning force may be produced by, for example, a spring, a weight, a solenoid or a hydraulic cylinder.

The substrate carrying the film may be moved by, for example, a belt, chain or wire arranged either to pull or to push the substrate past the stylus so that the stylus and the film exhibit relative movement during which the stylus moves through the film. As the substrate moves past the stylus, a rotary motion is imparted to the stylus because of the resistance to movement of the stylus through the film and this rotary motion can be restrained by means of a restoring spring. The distortion of this spring is a measure of the resistance to movement and this can be monitored by any conventional method such as by means of a strain gauge or by Hall effect sensors.

In the case where the resistance to movement is determined electrically, the electrical signals are preferably recorded as a trace on a chart recorder to give a permanent visible record of the curing characteristics of the film.

In each case, the film will be found to give a different reading when the stylus is moving through an uncured portion of the film to the case where the stylus is moving through a cured portion of the film. When the stylus is moving through uncured film, a fairly constant reading should be obtained and similarly a fairly constant, but different, reading should be obtained when the stylus is moving through the cured film. The onset of cure can be considered to occur when there is a deviation from the original constant reading and the completion of cure can be considered to occur when the final reading is constant. The actual point of cure can be defined to occur anywhere between these values or when the constant final reading is reached and will depend upon the interpretation placed on the system by the operator. However, it is particularly convenient to consider the point of cure to be the period from the start of cure to the state where the reading is half way between the uncured and fully cured readings. In addition to the time for the point of cure, the rate of change of the reading against time during the transition from the uncured to the cured state can be measured. In the case where the readings are shown on a chart recorder, this value will be the tangent of the angle of the slope between the reading for the uncured film and the reading for the cured film.

In a particularly preferred embodiment for use in the case where the film is subjected to radiation to cause curing, a radiation detector may be included which monitors and records the amount of radiation the film has received during curing. Preferably, the trace on the chart recorder will be marked at a preset amount of radiation to enable the cure point to be measured with respect to the amount of radiation received rather than with respect to linear time. In this way a comparison of different products or between the same product under different conditions can be made with respect to the amount of radiation received.

Any suitable radiation detector may be used. For example, the detector may include a photo diode monitoring the radiation directly. A commercially available detector which may be used is U/V Digital Radiometer 103 of Macam Photometrics Ltd., of Livingstone, Scotland. In the case where the apparatus is used to monitor the U/V drying of inks on a printing press, a particularly suitable radiation detector which may be used is one comprising a measuring head for positioning at the location where the radiation is to be detected and including a filter of the type which emits fluorescent light when exposed to ultraviolet radiation in an amount dependent on the amount of ultraviolet radiation to which it is exposed. The detector then additionally includes a means for detecting the amount of fluorescent light emitted to obtain a measure of the amount of ultraviolet radiation present at the location.

In an alternative embodiment, the amount of radiation present may be determined by monitoring the current/voltage applied to the lamps.

Ordinarily, in the case where the curing characteristics of a liquid film are being monitored the radiation source will be of relatively low power. However, in the case where the invention is used to determine the degree of cure of a film which has already been subjected to curing conditions, the radiation source may be of relatively high power. In this case, the film (which may perhaps have already been cured to an extent such that it is tack free) is irradiated and the change in resistance to motion of the stylus through the film is measured in accordance with the invention. If there is no change, the film was already fully cured. If there is a change, then the film had only been partially cured. This approach can also be used for investigating the phenomenon commonly referred to as "post cure" particularly of printing inks.

For a better understanding of the invention and to show how the same may be carried into effect, reference will now be made, by way of example, to the accompanying drawings, in which:

DETAILED DESCRIPTION OF THE DRAWINGS

Figure 1:
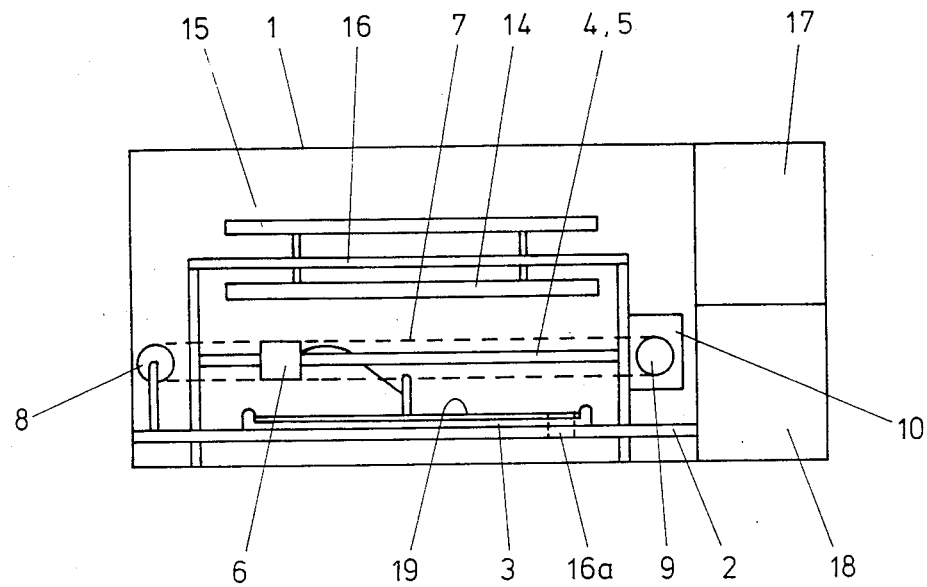
FIG. 1 is an elevation of one form of apparatus of the present invention.
Figure 2:
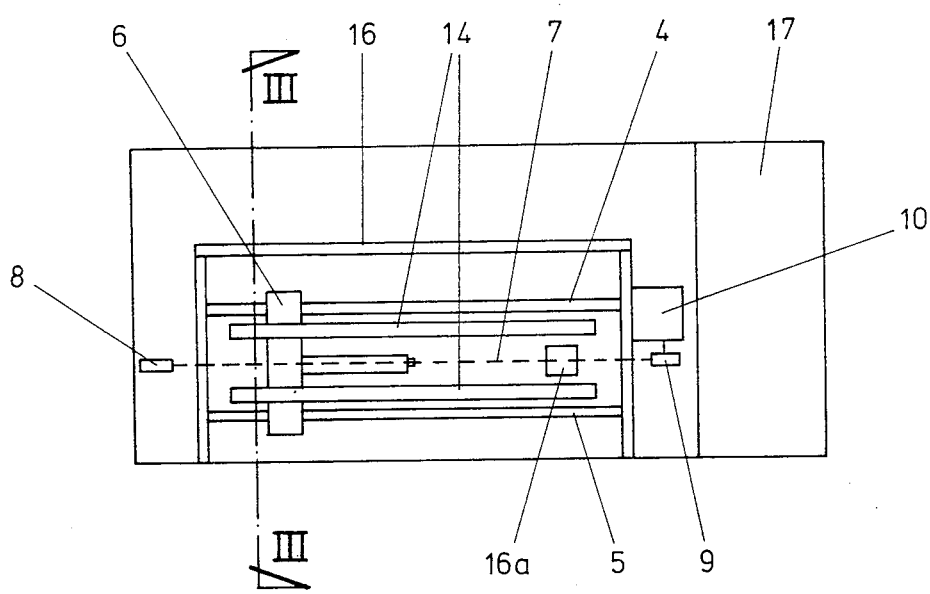
FIG. 2 is a plan view of the apparatus of FIG. 1.
Figure 3:
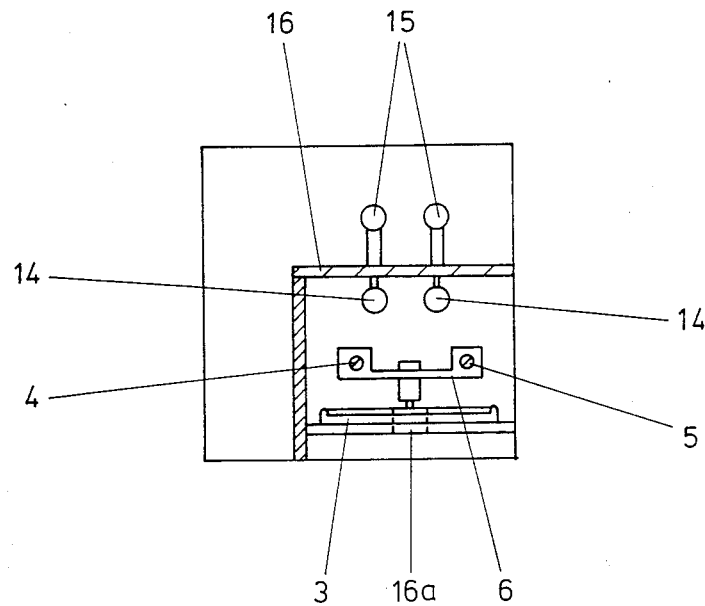
FIG. 3 is a cross section through the apparatus of FIG. 2 along line III—III.

Referring now to FIGS. 1 to 3, there is shown an apparatus comprising a generally rectanguloid casing 1 including an internal floor 2 for supporting a removeable tray 3 containing a substrate 19 carrying a wet film on its free surface. A pair of spaced parallel guide rails 4 and 5 is securely mounted within the casing 1 above the floor 2 and a carriage in the form of a cross-bar 6 is mounted on the guide rails 4 and 5 so as to be axially movable therealong. The carriage is connected to an endless wire (denoted by discontinuous line 7) passing over a freely rotating pulley 8 at one end of the casing 1 and passing over a pulley 9 driven by a motor 10 at the other end of the casing 1. Thus, on rotation of pulley 9 by motor 10, the carriage is caused to traverse from one end of the guide rails 4 and 5 to the other.

Figure 4:
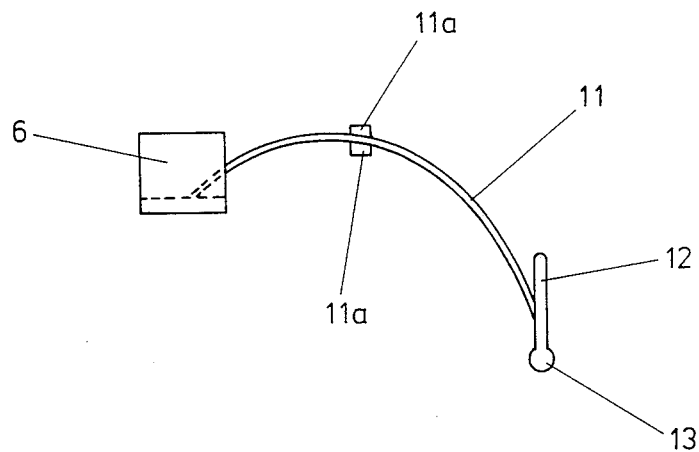
FIG. 4 is an elevation of a part of the apparatus of FIGS. 1 to 3 on an increased scale.
Figure 5:
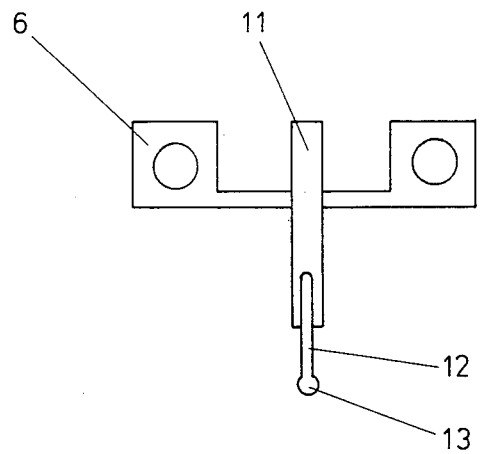
FIG. 5 is an end view of the part of FIG. 4.

The carriage is shown in more detail in FIGS. 4 and 5 from which it can be seen that the cross-bar 6 is connected to one end of a spring 11 having its other end connected to a stylus 12 formed of stainless steel and having a spherical lower end 13. The arrangement is such that the stylus 12 penetrates the liquid film on the substrate 19 so as to contact the surface of the substrate. Strain gauges 11a are mounted at either side of spring 11.

The apparatus includes a pair of ultraviolet lamps 14 located above the floor 2 so as to subject the film on the substrate 19 to radiation. The lamps 14 are mounted on one side of a slidable partition 16 which carries a further pair of lamps 15 on its other side. The film on the substrate 19 may be illuminated by either lamps 14 or 15, the choice being made by removing the partition 16 from the casing, inverting the same so that the desired lamps face the film, and replacing it in the casing. In this way, the power of the lamps or the wavelength of the radiation can be readily altered. The detector 16a of ultraviolet radiation is mounted in the casing at a similar level to the substrate 19.

The apparatus includes a control panel 17 including a means whereby the speed of rotation of the motor 10 may be preset and a means such as a variable choke or ballast resistance whereby the amount of radiation generated by the ultraviolet lamps 14 or 15 may be controlled. Also, the apparatus includes a chart recorder 18 which is operably connected by suitable circuitry to the strain gauges 11a attached to the spring 11.

In use, the carriage is positioned along the guide rails 4 and 5 in such a location that the stylus 12 penetrates through the liquid film at one end of the substrate 19 so as to contact the surface of the substrate. Then, after the desired amount of radiation and the speed of the motor 10 have been preset to the appropriate values, the motor 10 and lamps 14 (or 15) are actuated from the control panel so as to cause the carriage to move along the guide rails 4 and 5 with the stylus 12 being pushed or pulled through the film on the substrate 19 whilst it is curing as a consequence of being irradiated by the ultraviolet lamps 14 (15). As the film cures, the stylus encounters increased resistance to motion through the film and this causes the spring 11 to be deflected. The amount of deflection is monitored by the strain gauges and the readings exhibited by the strain gauges are shown as a trace on the chart recorder. The point of cure and the rate of cure can then be read off from the trace. Also, by noting the amount of radiation received by the film (by means of detector 16a), the curing characteristics of the film, as a function of the amount of radiation, can be determined.

Figure 6:
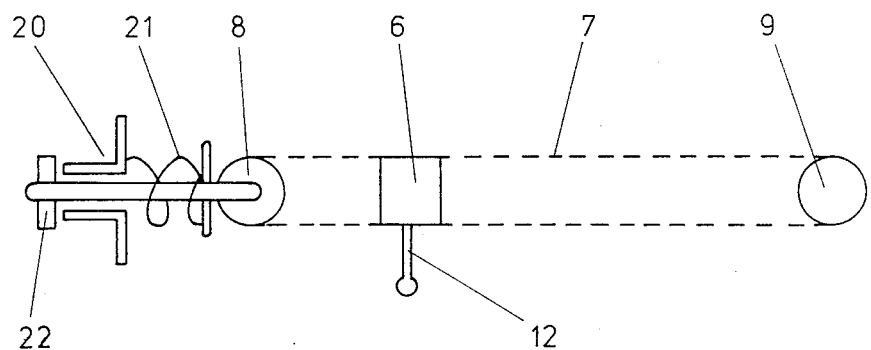
FIG. 6 is an elevation of a modification of a part of the apparatus of FIGS. 1 to 3.
Figure 7:
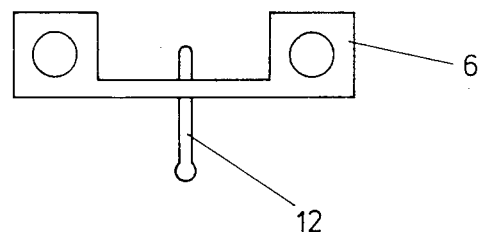
FIG. 7 is an end view of the modification shown in FIG. 6.

Referring now to FIGS. 6 and 7, there is shown part of a modified apparatus. Parts corresponding to parts of FIGS. 1 to 5 are denoted by like reference numerals. In this case, the stylus 12 is mounted directly on the crossbar 6 but the free wheeling pulley 8, instead of being fixedly mounted in the casing as in the case of FIGS. 1 to 5, is spring-loaded by being mounted on a telescopic member 20 the extension of which is controlled by spring 21. In this case, as the stylus 12 encounters resistance to motion as it is being pulled through the film by the wire 7, this will cause the pulley 8 to move axially towards pulley 9 by virtue of its spring-loaded mounting arrangement. In this case, the axial movement of pulley 8 is monitored by means of a piezoelectric device 22 which is operably connected to electrical circuitry and thence to the chart recorder 18 so that the resistance to movement of the stylus 12 through the film as the film cures under the influence of the ultraviolet lamps is shown as a trace on the chart recorder. Alternatively the axial movement may be monitored by, for example, strain gauges or the Hall effect.

Figure 9:
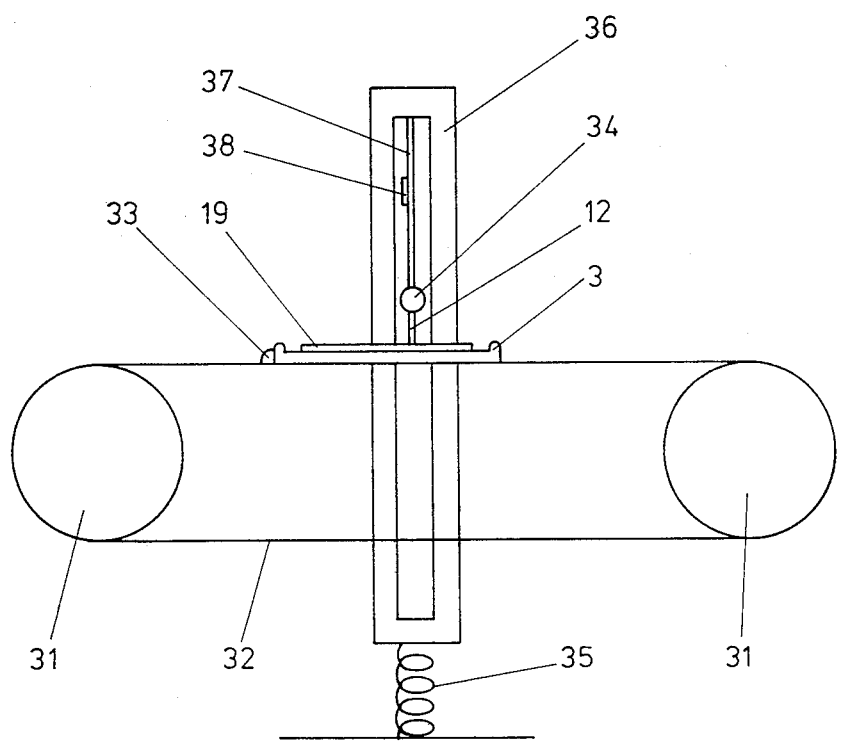
FIG. 9 is a diagrammatic elevation of part of another form of apparatus of the present invention.
Figure 10:
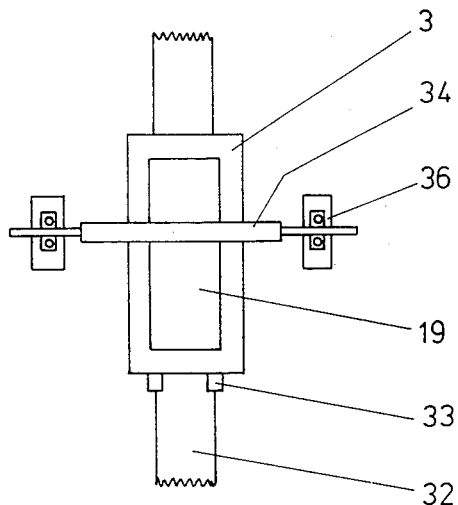
FIG. 10 is a diagrammatic plan view of part of the apparatus of FIG. 9.
Figure 11:
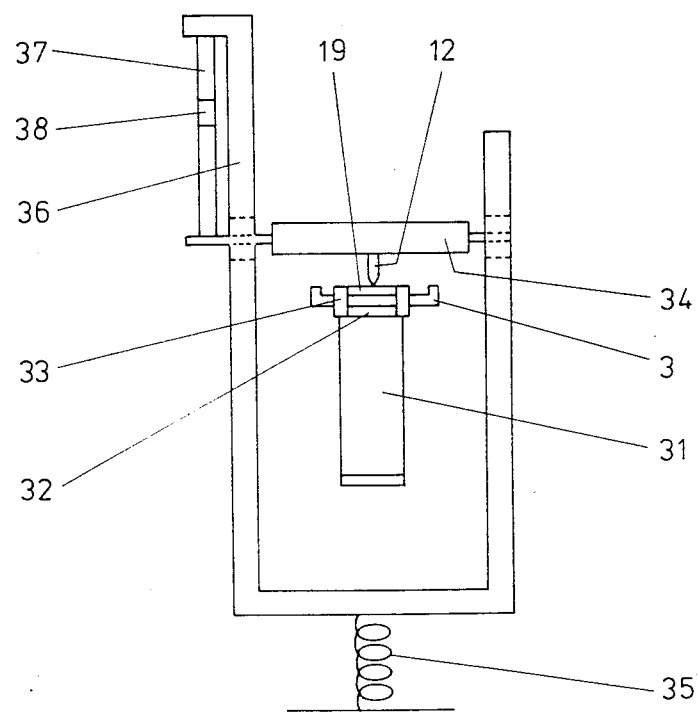
FIG. 11 is a diagrammatic end view of part of the apparatus of FIGS. 9 and 10.

Referring now to FIGS. 9 to 11, there is shown another form of the apparatus. Parts corresponding to parts of FIGS. 1 to 5 are denoted by like reference numerals.

In this case, the tray 3 containing the substrate 19 carrying the film is moved with respect to the stylus 12 which is stationary.

The apparatus includes a casing (not shown) and mounted in the casing is a pair of chain wheels 31 around which passes a chain 32 carrying drive dogs 33. The tray 3 is supported by the chain 32 and is driven past the stylus 12 by the drive dogs 33 as the chain wheels 31 are driven by a stepper motor (not shown). The stylus 12 is carried in an elongated holder 34 having ball bearings provided at each end whereby it can rotate about its longitudinal axis. The holder is mounted so that it can be displaced up and down in vertical slides mounted in a frame 36. The frame 36 is urged downwardly by means of a tensioning device 35 (e.g. a spring) so that the stylus 12 penetrates the film on the substrate. As the film moves past the stylus 12, the resistance to the movement of the stylus 12 through the film tends to cause the holder 34 to rotate and a restoring spring 37 carrying a strain gauge 38 or the like is provided to resist this rotation. The degree to which the restoring spring is distorted is a measure of the resistance to the movement of the stylus 12 through the film which in turn is a measure of the change in the rheological properties of the film as it solidifies. As in the previous embodiment, the apparatus will ordinarily include an assembly of ultraviolet lamps which can be inverted to facilitate altering the radiation, a control panel including a means whereby the speed of rotation of the motor for the chain wheels 31 may be preset and a means whereby the amount of radiation generated by the ultraviolet lamps may be controlled, and a chart recorder electrically connected to the strain gauge.

Figure 12:
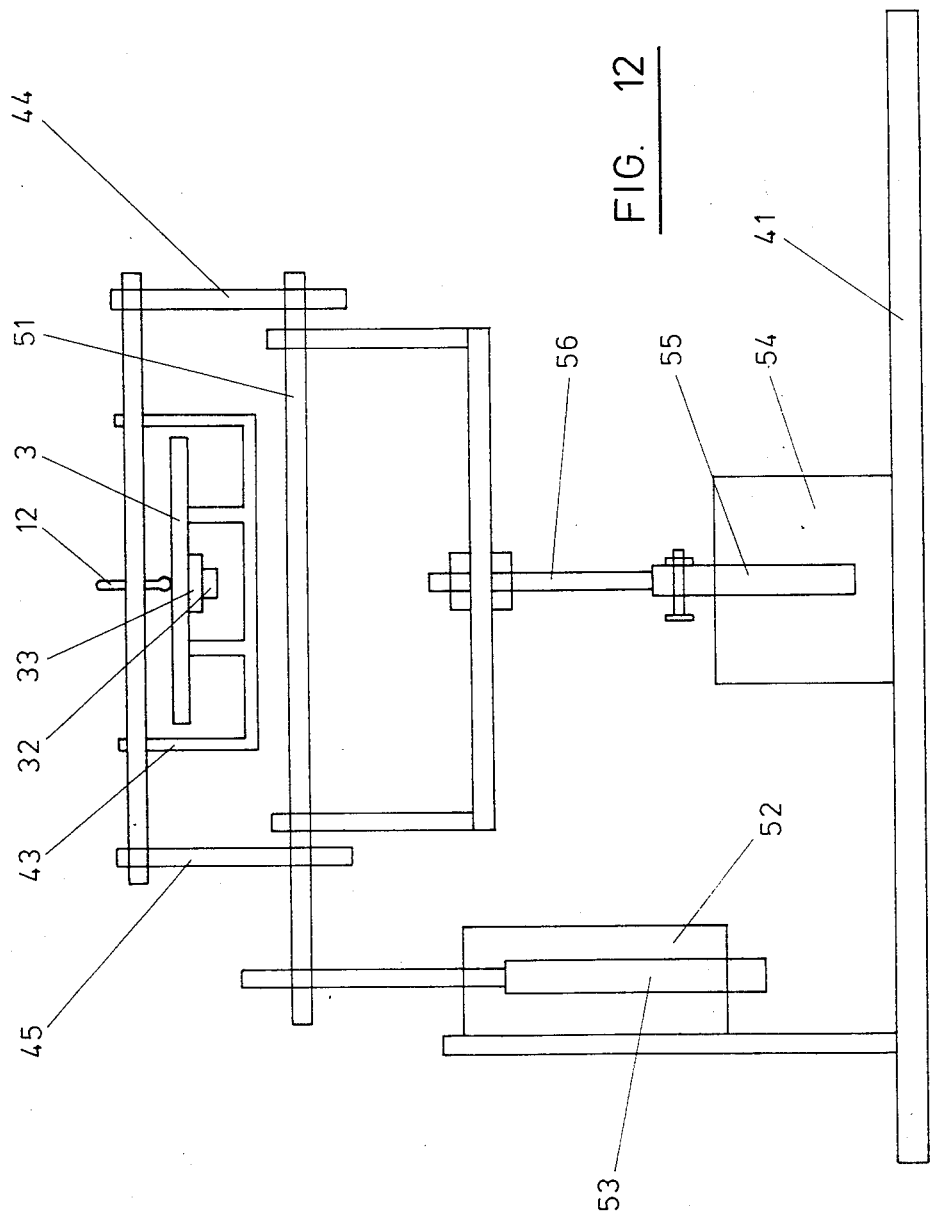
FIG. 12 is a diagrammatic cross-section through yet a further form of apparatus of the present invention.
Figure 13:
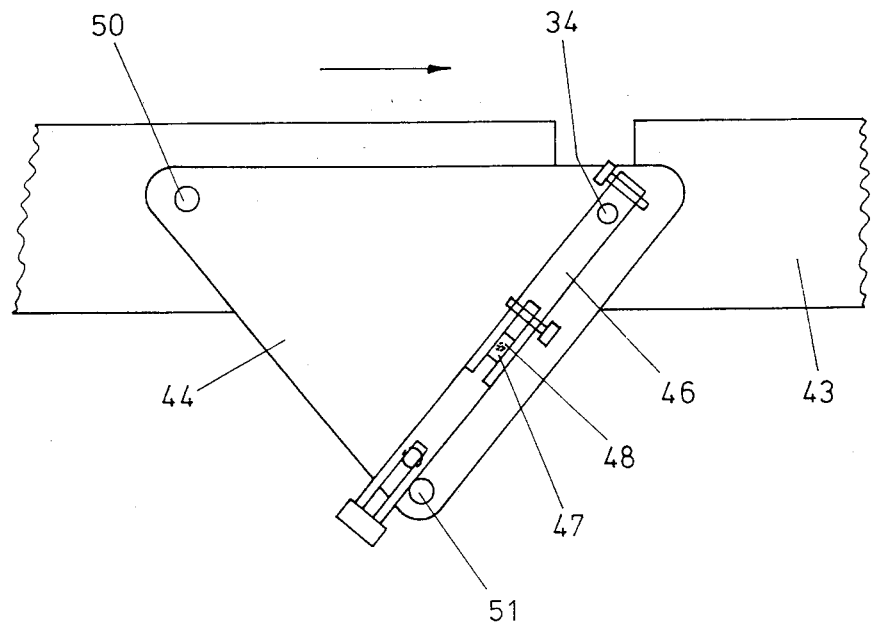
FIG. 13 is a schematic view of a part of the apparatus of FIG. 12 from one side.
Figure 14:
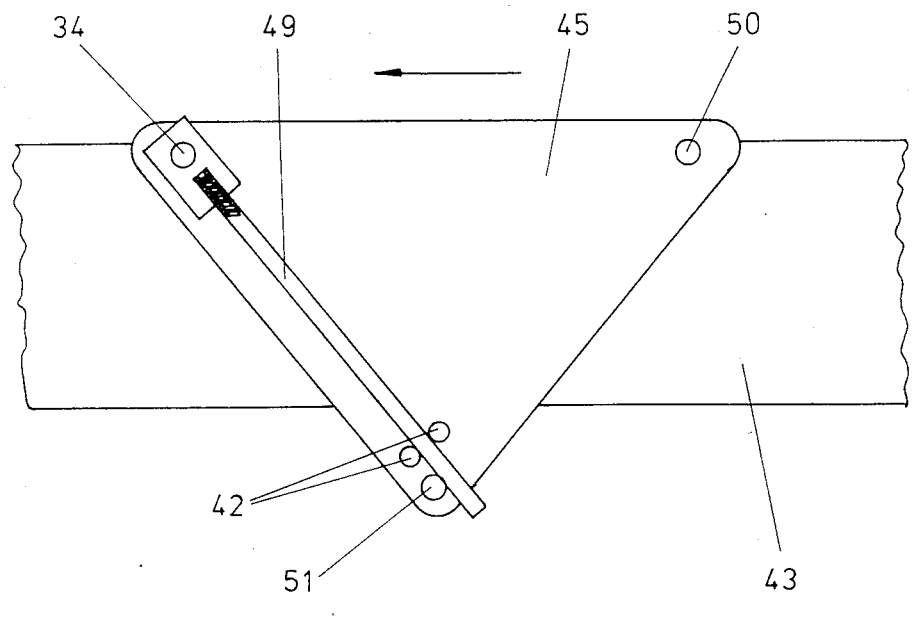
FIG. 14 is a schematic view of a part of the apparatus of FIG. 12 from the other side.

Referring now to FIGS. 12 to 14, parts corresponding to parts of FIGS. 9 to 11 are denoted by like reference numerals.

The apparatus comprises a baseboard 41 having supports (not shown in the interests of clarity) for a channel member 43 defining a path through the apparatus for the tray 3 carrying a substrate coated with the film to be tested (not shown). The tray 3 is moved along the path by the drive dog 33 on the chain 32, the chain 32 being driven by chain wheels and a stepper motor (not shown) in the manner of the apparatus of FIGS. 9 to 11. The holder 34 for the stylus 12 is mounted for rotation about its longitudinal axis in first and second side plates 44 and 45, respectively. A side arm 46 is connected to the end of the holder 34 extending through the side plate 44 and the side arm 46 includes a magnet 47 located above a Hall effect detector 48 capable of detecting displacement of the side arm as a consequence of rotational movement of the holder 34. The output from the Hall effect detector 48 is electrically connected to a chart recorder (not shown). A spring 49 is connected to the end of the holder 34 extending through the side plate 45 and is located between a pair of clips 42 to prevent any movement of the spring other than a bending movement as the holder 34 is angularly displaced about its axis. The spring 49 restores the holder 34 to its start position after it has been angularly displaced as a consequence of the stylus 12 moving through the film on the substrate. The side plates 44 and 45 are pivotally mounted on the channel member 43 about shaft 50 and are connected together by a cross bar 51. The apparatus includes a first solenoid 52 having an armature 53 connected to the cross bar 51. The solenoid 52 is vertically adjustable with respect to the baseboard 41 and acts to angularly displace the side plates 44 and 45 about shaft 50 so as to lift the stylus 12 off the coated substrate. A second solenoid 54 is mounted on the baseboard 41 and has an armature 55 connected to the cross bar 51 by an adjustable linkage 56. This solenoid operates in the direction contrary to solenoid 52 and acts to angularly displace the side plates 44 and 45 about shaft 50 so that the stylus 12 penetrates the film on the substrate. A means (not shown) is provided to enable the amount of current passing through the solenoid 52 to be preset to a desired amount whereby the pressure to be exerted by the stylus 12 can be selected as desired.

In a manner similar to the apparatus of FIGS. 9 to 11, the apparatus includes an assembly of invertable ultraviolet lamps, a control panel including a means whereby the speed of rotation of the drive motor for the chain 32 may be preset, a means whereby the lamps become illuminated after a presettable delay, a means for varying the pressure exerted by the stylus 12, and a means whereby the amount of radiation generated by the ultraviolet lamps may be controlled. These have, however, been omitted in the interests of clarity.

In use, a coated substrate is placed on the tray 3 and is moved by the chain 32 with respect to the stylus 12 at an appropriate speed in the direction indicated by the arrows in FIGS. 13 and 14. The second solenoid 55 is actuated to pull the stylus 12 down into the coating of the substrate.

The movement of the stylus 12 through the coating as the substrate passes through the apparatus causes the holder 34 to be angularly displaced with respect to the side plates 44 and 45 and the extent to which this displacement occurs is a measure of the degree to which the coating has solidified. The displacement of the holder 34 is measured by the Hall effect detector 48 and displayed as a trace on the chart recorder. After a desired time interval, which may be preset, the first solenoid 51 is actuated to lift the stylus 12 off the coated substrate.

The following Examples illustrate the invention.

EXAMPLE 1

Figure 8:
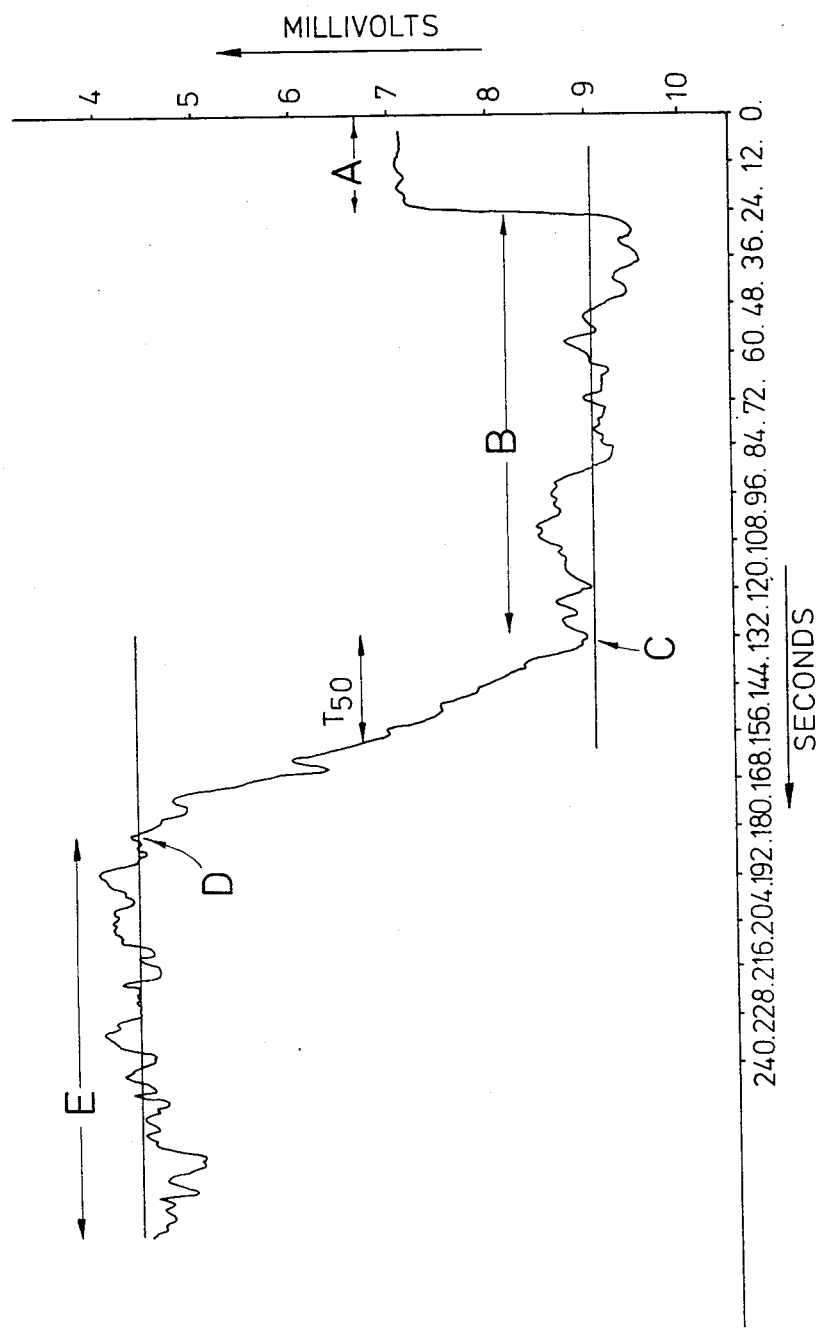
FIG. 8 is a graph showing the relationship between curing time and resistance to motion of the stylus through a film of ink as it cures under the influence of ultraviolet radiation.

A substrate of carton card coated with an ultraviolet light curable ink was mounted on the tray 3 of an apparatus as shown in FIGS. 1 to 5. The motor 10 was preset so as to move the member 6 at a speed of 3.3 cms/min and the lamps 14 were preset to an intensity of 15W each at a wavelength of 254 nm. The motor 10 and the lamps 14 were then actuated and the resistance to motion of the stylus 12 through the film was monitored as the film was cured under the influence of the ultraviolet radiation. The results were recorded as a trace on the chart recorder 18 and are shown graphically in FIG. 8.

Region A corresponds to the case where the stylus was moving across an area of the substrate which was uncoated with ink. Once the stylus reaches the uncured liquid ink, this provides a lubricant effect and the resistance to motion of the stylus decreases (region B). The lamps were switched on at point C and it can be seen that the resistance to motion increases as the ink becomes fully cured at point D. Region E corresponds to the case where the stylus is passing through the cured solid ink film. Under the conditions employed, the point of cure occurred at 26 seconds and the rate of cure corresponds to about 1 mv/sec.

EXAMPLE 2

This illustrates the use of the apparatus of FIGS. 12 to 14 to determine the solidification characteristics of an epoxy resin film which cures by chemical reaction. The epoxy resin used was Araldite Rapid manufactured by Ciba-Geigy Plastics of Duxford, Cambridge, U.K. This is a two-component product consisting of an adhesive and a hardener. The instructions for use suggest mixing equal amounts of adhesive and hardener and applying the mixture to the object to be glued. The initial set should occur in 10 minutes, it should take from ½ to 1 hour to harden, and full strength should be achieved in 8 hours.

Equal amounts of the adhesive and hardener were mixed and applied by a coater to a glass substrate to produce a uniform layer of about $76 \times 10^{-6}$ meters thickness.

The coating was tested at room temperature using the apparatus without the U.V. lamps being illuminated. The substrate was moved past the stylus at a speed of 1 cm/min.

Figure 15:
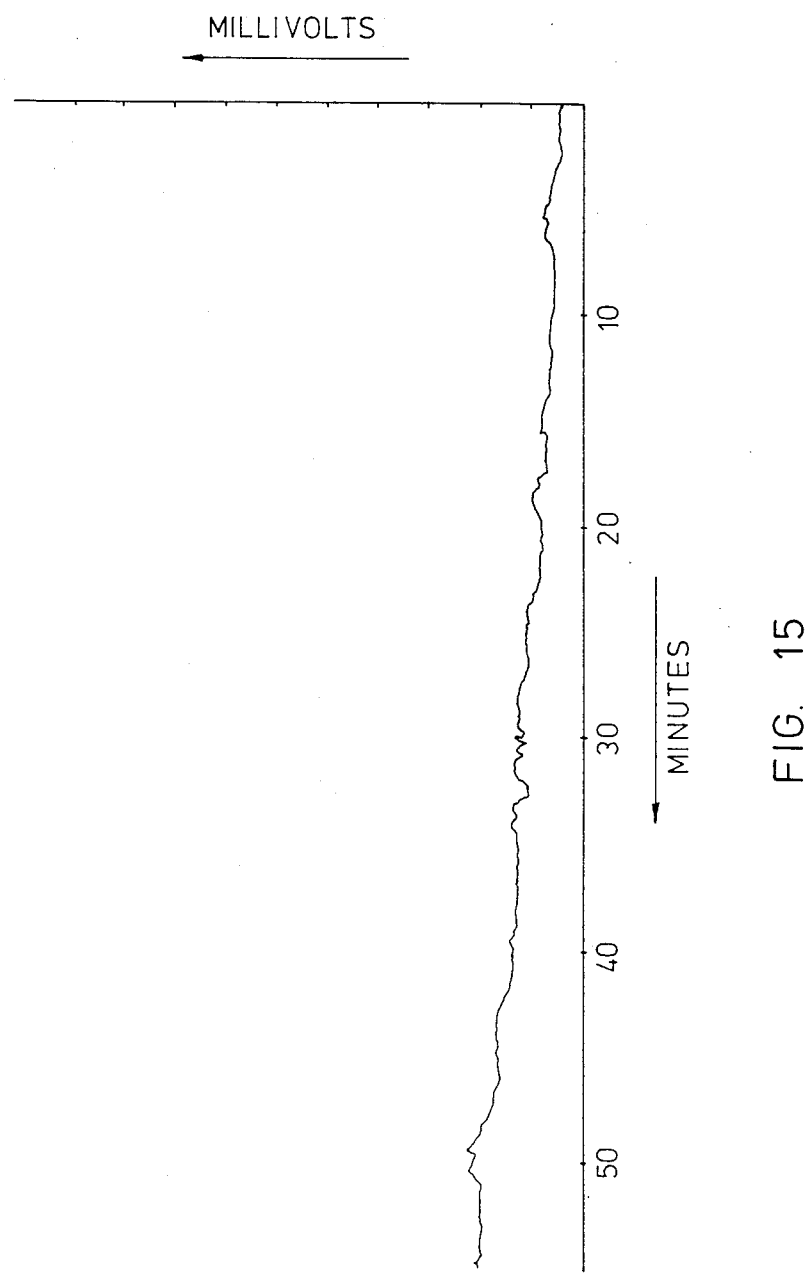
FIG. 15 is a graph showing the relationship between curing time and resistance to motion of the stylus through a film of epoxy resin as it cures at room temperature.

The trace obtained on the chart recorder is shown in FIG. 15. A slow increase in signal can be seen until a relatively constant value was obtained after 45 to 50 mins had elapsed. The film, at this time, was hard, but could be easily marked by a thumb-nail.

EXAMPLE 3

Figure 16:
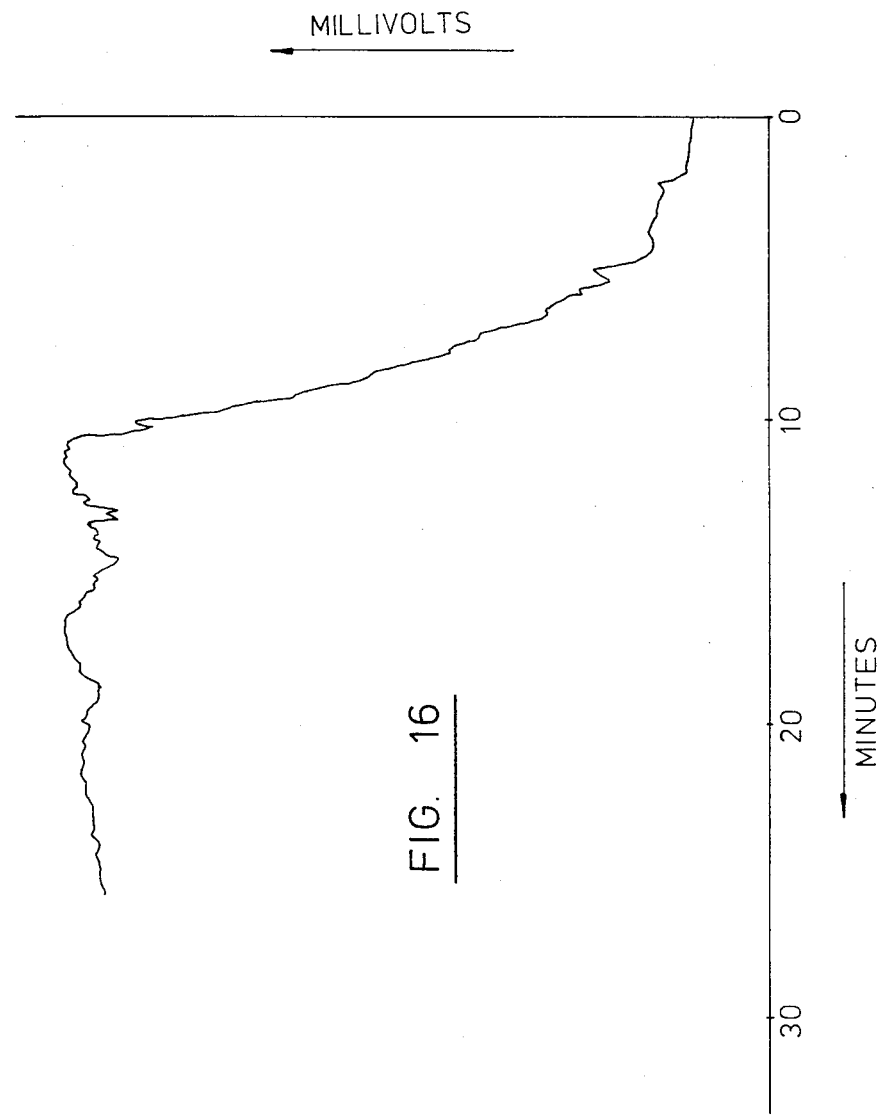
FIG. 16 is another graph showing the relationship between curing time and resistance to motion of the stylus through a film of epoxy resin as it cures at elevated temperature.

Example 2 was repeated but in this case the U.V. lamp assembly of the apparatus was removed and replaced by two infra-red lamps. The trace obtained on the chart recorder is shown in FIG. 16. It shows a rapid increase in signal until a plateau value is reached after 10 to 12 minutes. The signal then remains at this value. The film at this time was hard and could not be marked by a thumb-nail.

EXAMPLE 4

This illustrates the use of the apparatus of FIGS. 12 to 14 to determine the solidification characteristics of a film which cures by solvent evaporation. The film was a film of Bostik All Purpose Clear Adhesive manufactured by Bostik Limited, Leicester, U.K. and containing acetone as solvent.

The adhesive was applied by a coater to a glass substrate to produce a uniform layer of about $76 \times 10^{-6}$ meters (when wet) thickness. The coating was tested at room temperature using the apparatus without the U.V. lamps being illuminated. The substrate was moved past the stylus at a speed of 1 cm/min.

Figure 17:
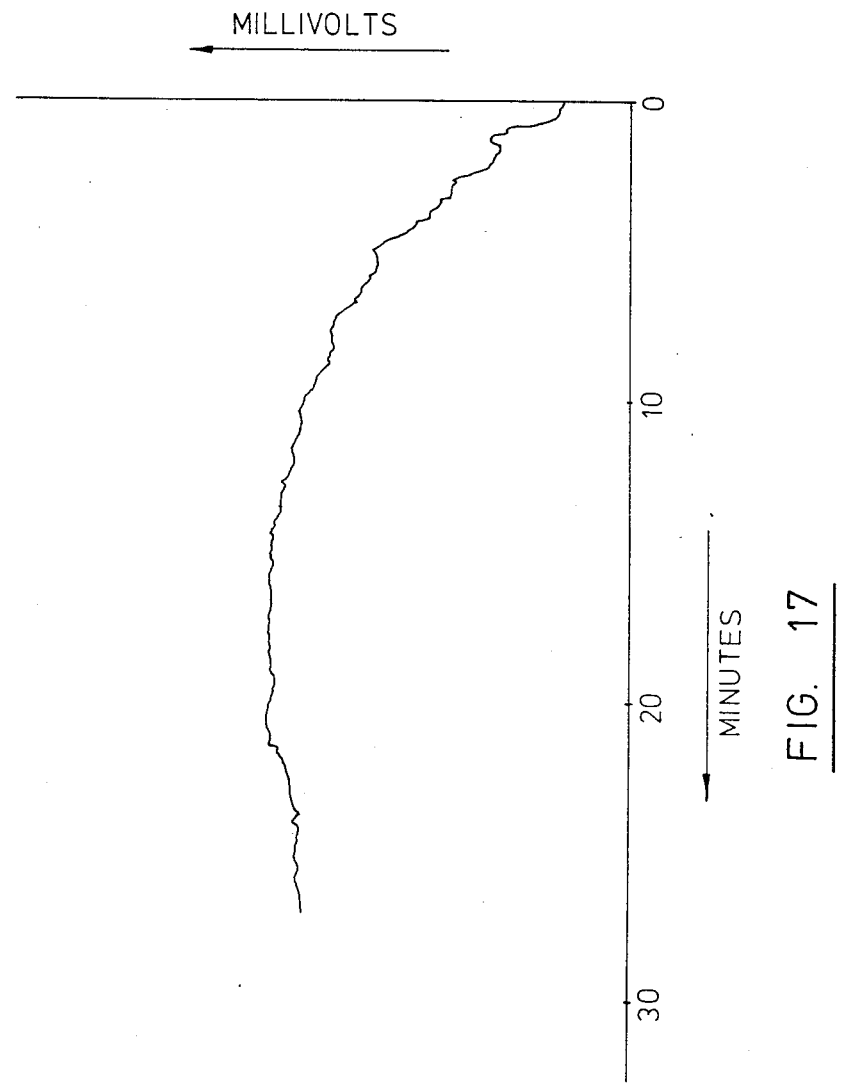
FIG. 17 is a further graph showing the relationship between curing time and the resistance to motion of the stylus through a film of solvent based adhesive at room temperature.

The trace obtained on the chart recorder is shown in FIG. 17. A steadily rising signal can be seen levelling off to a constant value after 15 to 20 minutes. The layer at this time was hard and could not be easily marked by a thumb-nail.

EXAMPLE 5

Two different but conventional overprinting varnish lacquers (A and B) were coated onto aluminised cardboard and the solidification characteristics of the coatings were monitored using the apparatus shown in FIGS. 12 to 14. The mid points of cure (T50) were as follows:

Lacquer A 22 seconds
Lacquer B 28 seconds.

The experiment was repeated with the lacquers coated onto cardboard which had been coated with black ink. The mid points of cure (T50) were as follows:

Lacquer A 68 seconds
Lacquer B 48 seconds.

Thus the relative cure rates of the lacquers were reversed by changing the substrate.

We claim:

1. An apparatus for monitoring the solidification characteristics of a solidifiable liquid film coated onto the surface of a substrate which apparatus comprises:
   (i) a means of supporting the coated substrate whilst the film is solidifying,
   (ii) a stylus mounted so as to penetrate the liquid film and contact the surface of the substrate,
   (iii) a means of effecting relative movement between the stylus and the substrate so that the stylus moves with respect to the surface of the substrate and through the film whilst the film is solidifying, and
   (iv) means of monitoring the resistance to movement of the stylus through the film to obtain a measure of the solidification characteristics of the film.

2. An apparatus as claimed in claim 1 which includes a means of subjecting the film to ultraviolet radiation or to elevated temperature.

3. An apparatus as claimed in claim 2 and including a radiation detector to monitor the amount of radiation received by the film.

4. An apparatus as claimed in claim 2 wherein a means is provided to move the coated substrate with respect to the stylus.

5. An apparatus as claimed in claim 4 wherein the stylus is mounted in a holder supported so as to be able to move perpendicularly with respect to the coated surface and the apparatus includes a means of applying a tensioning force to the holder so as to cause the stylus to penetrate the film.

6. An apparatus as claimed in claim 5 wherein the means of applying the tensioning force is a solenoid.

7. An apparatus as claimed in claim 1 wherein the means of monitoring the resistance to movement produces an electrical signal and the apparatus includes a chart recorder for recording the signal as a trace.

* * * * *